us010988580B2

(12) United States Patent
Hori et al.

(10) Patent No.: US 10,988,580 B2
(45) Date of Patent: Apr. 27, 2021

(54) SILICONE PARTICLES, AND COSMETIC, COATING, AND RESIN FORMULATED USING SAME

(71) Applicant: Dow Corning Toray Co., Ltd., Tokyo (JP)

(72) Inventors: Seiji Hori, Chiba (JP); Yasue Kanzaki, Chiba (JP); Hiroko Taniguchi, Chiba (JP); Mari Wakita, Chiba (JP)

(73) Assignee: Dow Toray Co., Ltd., Tokyo (JP)

( * ) Notice: Subject to any disclaimer, the term of this patent is extended or adjusted under 35 U.S.C. 154(b) by 42 days.

(21) Appl. No.: 16/097,911

(22) PCT Filed: Apr. 27, 2017

(86) PCT No.: PCT/JP2017/016648
§ 371 (c)(1),
(2) Date: Oct. 31, 2018

(87) PCT Pub. No.: WO2017/191798
PCT Pub. Date: Nov. 9, 2017

(65) Prior Publication Data
US 2019/0144612 A1    May 16, 2019

(30) Foreign Application Priority Data
May 2, 2016    (JP) .............................. JP2016-092759

(51) Int. Cl.
| | | |
|---|---|---|
| *C08G 77/50* | (2006.01) | |
| *A61K 8/891* | (2006.01) | |
| *A61Q 1/12* | (2006.01) | |
| *A61Q 19/00* | (2006.01) | |
| *A61Q 1/02* | (2006.01) | |
| *A61Q 17/04* | (2006.01) | |
| *C08G 77/08* | (2006.01) | |
| *C08L 83/14* | (2006.01) | |
| *C09D 7/65* | (2018.01) | |
| *C09D 7/40* | (2018.01) | |

(52) U.S. Cl.
CPC .............. *C08G 77/50* (2013.01); *A61K 8/891* (2013.01); *A61Q 1/02* (2013.01); *A61Q 1/12* (2013.01); *A61Q 17/04* (2013.01); *A61Q 19/00* (2013.01); *C08G 77/08* (2013.01); *C08L 83/14* (2013.01); *A61K 2800/412* (2013.01); *C08L 2312/08* (2013.01); *C09D 7/65* (2018.01); *C09D 7/69* (2018.01)

(58) Field of Classification Search
CPC ........ C08G 77/50; C08G 77/12; C08G 77/20; C08L 83/04
See application file for complete search history.

(56) References Cited

U.S. PATENT DOCUMENTS

| 5,665,804 | A | 9/1997 | Hill et al. |
|---|---|---|---|
| 6,476,123 | B1 | 11/2002 | Morita et al. |
| 6,531,542 | B1 * | 3/2003 | Morita ..................... A61K 8/86 |
| | | | 523/340 |
| 2004/0171699 | A1 * | 9/2004 | Morita ................... C08K 5/103 |
| | | | 516/9 |
| 2009/0098080 | A1 | 4/2009 | Ando et al. |
| 2010/0158824 | A1 | 6/2010 | Lin |
| 2010/0172849 | A1 | 7/2010 | Shaow et al. |
| 2010/0183525 | A1 | 7/2010 | Lin |
| 2011/0105627 | A1 | 5/2011 | Ando et al. |
| 2012/0232202 | A1 | 9/2012 | Morita |
| 2014/0364394 | A1 * | 12/2014 | Tamura .................... A61Q 5/02 |
| | | | 514/63 |
| 2015/0306019 | A1 | 10/2015 | Wakita |
| 2018/0215877 | A1 | 8/2018 | Seiji Hai et al. |

FOREIGN PATENT DOCUMENTS

| JP | 2000034205 | A | | 2/2000 |
|---|---|---|---|---|
| JP | 2001040214 | A | | 2/2001 |
| JP | 2009530477 | A | | 8/2009 |
| JP | 4371480 | B2 | | 9/2009 |
| JP | 2011219547 | | * | 11/2011 |
| JP | 2011219547 | A | | 11/2011 |
| JP | 5185111 | B2 | | 1/2013 |
| JP | 2014122316 | A | | 7/2014 |
| JP | 2015113303 | A | | 6/2015 |
| WO | WO2017018358 | A1 | | 2/2017 |

OTHER PUBLICATIONS

JP 2011 219547 machine translation (2011).*
PCT/JP2017/016648 International Search Report dated Aug. 1, 2017, 4 pages.
English language abstract and machine translation for JP2000034205 (A) extracted from https://worldwide.espacenet.com database on Nov. 27, 2018, 25 pages.

(Continued)

*Primary Examiner* — Kuo Liang Peng
(74) *Attorney, Agent, or Firm* — Warner Norcross + Judd LLP

(57) ABSTRACT

Silicone particles having excellent dispersibility are provided. A cosmetic material having excellent feeling of use, and a highly functional paint and an electronic material are also provided.

The silicone particles include a siloxane as a component. A content of a hydrogen atom bonded to a silicon atom per unit mass is 300 ppm or less. In addition, the silicon atom in the siloxane as a component for the silicone particles is crosslinked with another silicon atom via an alkylene group having a carbon number of 4 to 20.

10 Claims, No Drawings

(56) References Cited

OTHER PUBLICATIONS

English language abstract and machine translation for JP2011219547 (A) extracted from https://worldwide.espacenet.com database on Nov. 27, 2018, 29 pages.
English language abstract and machine translation for JP2015113303 (A) extracted from https://worldwide.espacenet.com database on Nov. 27, 2018, 50 pages.

* cited by examiner

SILICONE PARTICLES, AND COSMETIC, COATING, AND RESIN FORMULATED USING SAME

CROSS-REFERENCE TO RELATED APPLICATIONS

This application is the National Stage of International Application No. PCT/JP2017/016648 filed on 27 Apr. 2017, which claims priority to and all advantages of Japanese Patent Appl. No. 2016-092759 filed on 2 May 2016, the content of which is hereby incorporated by reference.

TECHNICAL FIELD

The present invention relates to silicone particles having low aggregation over time and high lipophilicity without blending a third component such as inorganic fine particles and silsesquioxane particles. The present invention relates to a cosmetic material containing silicone particles having excellent feeling in use, and a cosmetic raw material thereof, and a paint and a resin compounding agent.

BACKGROUND ART

Silicone particles are used as additives for cosmetic materials, paints, inks, thermosetting organic resins, thermoplastic organic resins and the like. In particular, silicone particles are suitably used as stress relieving agents for thermoplastic organic resins or as surface lubricants for organic resin films.

Silicone particles are obtained by curing an addition reaction-curable silicone composition or a condensation reaction-curable silicone composition. The particle size and the oil absorption properties vary depending on the method for producing thereof. In general, when granules are produced by crushing a cured product, the miniaturization is limited. Therefore, a method for producing silicone particles having a small particle size by curing reaction of a particulate matter of the crosslinkable silicone composition is preferred.

However, even if the primary particles are fine, they tend to aggregate over time into the secondary particles. Further, the aggregated particles are not easily redispersed to form the primary particles. This is due to the phenomenon that once the primary particles are bonded together as aggregated particles, the bond is less likely to split (dissociate).

Disclosed was a method for adding and curing an organic compound having an aliphatic unsaturated bond such as hexadiene or cyclohexanedimethanol divinyl ether during the formation of silicone particles in order to be useful as cosmetic raw materials. (JP Patent No. 4371480.) However, when this method is used, the organic compound is not sufficiently incorporated into silicone particles, and if unreacted SiH is used as a residue, then the particles may aggregate over time.

When silicone particles having strong aggregation properties are blended in a solvent, the silicone particles having the primary particle size themselves are not dispersed, and the particles become secondary aggregated particles or a larger agglomerate thereof. The problem is that the dispersion is insufficient and a uniform mixture cannot be prepared from them. Therefore, there is a problem that the composition containing silicone particles cannot fully exhibit the characteristics of silicone particles. In general, it is known that particles having low hardness, such as silicone rubber granules, tend to aggregate over time.

It is also known that such aggregation over time affects the oil absorption properties of silicone particles. There is a problem of how to control this oil absorption properties for using as cosmetic products. Therefore, attempts have been made to control this oil absorption properties by controlling the temperature after production. (JP Patent No. 5185111) However, there was a big problem in that a control period is required after production.

Previously, vinyl groups have been used as alkenyl groups in the preparation of silicone particles. The use of a vinyl group is extremely advantageous to reduce cost and to estimate more easily the shape of silicone particles after the reaction. However, there has been a fundamental problem in that even if the improvement is achieved with silicone particles using the vinyl group, solutions have not been made with respect to the various problems as described above.

CITATIONS LIST

Patent Literature

Patent Literature 1: Japanese Patent No. 4371480
Patent Literature 2: Japanese Patent No. 5185111
Patent Literature 3: Japanese Unexamined Patent Application No. 2014-122316

SUMMARY OF INVENTION

Technical Problems

An object of the present invention is to provide silicone particles having excellent dispersibility, high lipophilicity and high storage stability, and a suitable method for producing thereof. Another object of the present invention is to provide a cosmetic material having excellent feeling of use, a resin having high functionality, and raw materials thereof.

Solutions to Problems

In silicone particles according to one embodiment of the present invention, the content of the hydrogen connected to the silicon atom per unit mass is 300 ppm or less, and the silicon atom in the siloxane that is a component for silicone particles is crosslinked with the other silicon atom via an alkylene group having a carbon number of 4 to 20.

The cosmetic raw material and the resin compounding agent according to one embodiment of the present invention is composed of the above-mentioned silicone particle. The cosmetic product, the paint and the electronic material contains the above-mentioned silicone particle.

The crosslinkable composition for forming silicone particles according to one embodiment of the present invention includes components (A) and (C) below:
(A) an organopolysiloxane having two or more alkenyl groups having 4 or more and 20 or less carbon atoms in one molecule; and
(B) a silicon organic compound having two or more hydrogen atoms connected to the silicon atom in one molecule, with the hydrogen atoms being not more than 40% based on the number of silicon atoms in one molecule, and/or
a silicon organic compound having two or more hydrogen atoms connected to the silicon atom in one molecule and having a trifunctional siloxane unit or a tetrafunctional siloxane unit;

wherein the molar ratio of the content of the alkenyl group (Alk) in the component (A) to the content of the hydrogen atom (H) connected to the silicon atom in the component (B) is:

H/Alk=0.7 to 1.2.

The method for producing silicone particles according to one embodiment of the present invention includes emulsifying the composition as described above and curing the composition in the presence of a catalyst.

Advantageous Effects of Invention

The silicone particles according to one embodiment of the present invention have low aggregation over time and high storage stability. In addition, silicone particles themselves have a pleasant tactile sensation, and have a characteristic that the feeling of use of cosmetics and the function of paints, resins and electronic materials can be improved. In addition, the composition according to one embodiment of the present invention can provide silicone particles. Further, the method for producing silicone particles, which is one embodiment of the present invention, is characterized in that such silicone particles can be produced efficiently.

DESCRIPTION OF EMBODIMENTS

Hereinafter, silicone particles of the present invention, a method for producing thereof, and cosmetics, paints and resins using the same will be described in detail.

In silicone particles according to one embodiment of the present invention, the content of the hydrogen connected to the silicon atom per unit mass is 300 ppm or less, and the silicon atom in the siloxane as a component for silicone particles is crosslinked with the other silicon atom via an alkylene group having a carbon number of 4 to 20.

The content of the hydrogen connected to the silicon atom in silicone particles according to one embodiment of the present invention is preferably 300 ppm or less, more preferably 250 ppm or less, and further preferably 200 ppm or less. Furthermore, the content is preferably 150 ppm or less, preferably 100 ppm or less, preferably 50 ppm or less, and further preferably 20 ppm or less. In this embodiment, if the content of the hydrogen connected to the silicon atom is increased, the hydrogen is crosslinked with other silicone particles to aggregate over time. In addition, in this embodiment, since there remains the hydrogen connected to the silicon atom in the silicone particle, hydrogen gas is generated during storage. By reducing or eliminating the generation of hydrogen gas, there is an advantage that silicone particles can be manufactured more safely.

As a method for measuring the hydrogen connected to the silicon atom in the silicone particle, a typical method is one using a gas chromatography (headspace method). For example, the hydrogen can be identified by adding an equivalent solution of potassium hydroxide in ethanol at a concentration of 40% to the unit mass of the silicone particle, standing the mixture for 1 hour, collecting the generated hydrogen gas until the reaction is completed, and quantitating by a headspace gas chromatography.

Preferably, the alkylene group which is crosslinked between the silicon atom in the siloxane as the component for silicone particles of the present invention and the other silicon atom has a carbon number of 4 to 20. The carbon number is more preferably 5 or more, 6 or more. On the other hand, the number is 16 or less, 12 or less, and 8 or less.

Silicone particles according to one embodiment of the present invention can be produced by reacting a composition including components (A) and (B) below:
(A) an organopolysiloxane having two or more alkenyl groups having 4 or more and 20 or less carbon atoms in one molecule; and
(B) a silicon organic compound having two or more hydrogen atoms connected to the silicon atom in one molecule, with the hydrogen atoms being not more than 40% based on the number of silicon atoms in one molecule, and/or
a silicon organic compound having two or more hydrogen atoms connected to the silicon atom in one molecule and having a trifunctional siloxane unit or a tetrafunctional siloxane unit, wherein
the molar ratio of the content of the alkenyl group (Alk) in the component (A) to the content of the hydrogen atom (H) connected to the silicon atom in the component (B) is:

H/Alk=0.7 to 1.2.

Examples of the alkenyl group having 4 or more and 20 or less carbon atoms in the component (A) include a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, and an icosenyl group. From the viewpoint of the reactivity, the carbon number of the alkenyl group is preferably 5 or more, and more preferably 6 or more. Similarly, from the viewpoint of the reactivity and aggregation properties, the carbon number of the alkenyl group is preferably 16 or less, more preferably 12 or less, and further preferably 8 or less. In particular, the alkenyl group is preferably a hexenyl group. The alkenyl group is preferably at the molecular chain terminal of the organopolysiloxane, but may be present on the side chain or both. Examples of the group connected to the silicon atom other than the alkenyl group include a substituted or unsubstituted monovalent hydrocarbon group, including an alkyl group such as a methyl group, an ethyl group, a propyl group and a butyl group; a cycloalkyl group such as a cyclopentyl group and a cyclohexyl group; an aryl group such as a phenyl group, a tolyl group, and a xylyl group; an aralkyl group such as a benzyl group, a phenethyl group and a 3-phenylpropyl group; and a halogenated alkyl group such as a 3-chloropropyl group and a 3,3,3-trifluoropropyl group. Examples of the molecular structure of the group include straight chain, cyclic, network and straight chain having partly branched chain. Particularly preferred are straight chain and straight chain having partly branched chain. In addition, this viscosity is preferably such that the hydrosilylation reaction crosslinkable silicone composition can be dispersed in water. Specifically, the viscosity is preferably in the range of 20 to 100,000 mPa·s at 25° C., and particularly preferably in the range of 20 to 10,000 mPa·s.

Further, from the viewpoint of the oil absorption properties of the resulting silicone powder, in the organopolysiloxane of the component (A), the content of the dimethylsiloxane unit represented by the formula: —(CH3)2SiO— is preferably 90 mol % or more based on the total siloxane units other than the siloxane unit at the terminal of the molecule. Similarly, from the viewpoint of improving the oil absorption properties of the resulting hydrosilylation reaction-crosslinkable silicone rubber powder, preferably a cyclic or chain organopolysiloxane having a low polymerization degree (degree of polymerization is 3 to 20) is previously removed by stripping and the like.

The content of the alkenyl group in the component (A) is preferably 0.50% by weight or more in one molecule of the organopolysiloxane, more preferably 0.60% by weight or more, further preferably 0.70% by weight or more, further preferably 0.80% by weight or more, and further preferably 0.90% by weight or more in one molecule of the organopolysiloxane. On the other hand, the upper limit is more preferably 5% by weight or less, and further preferably 4% by weight or less.

The component (B) is (i) a silicon organic compound having two or more hydrogen atoms connected to the silicon atom in one molecule, wherein the hydrogen atoms are not more than 40% based on the number of silicon atoms in one molecule; and/or (ii) a silicon organic compound having two or more hydrogen atoms connected to the silicon atom in one molecule and having a trifunctional siloxane unit or a tetrafunctional siloxane unit. The silicon organic compound (i) preferably has two or more hydrogens connected to the silicon atom in one molecule. The number of the hydrogen atoms connected to the silicon atom in one molecule is preferably not more than 40% based on the number of silicon atoms in one molecule, more preferably not more than 30%, not more than 25%, not more than 20%, not more than 15%, and further preferably not more than 10%. With respect to the silicon organic compound (ii), by having the trifunctional siloxane unit or the tetrafunctional siloxane unit, even if the unreacted portion of SiH remains, the aggregation of silicone particles over time is hardly affected due to the stereostructure. From the viewpoint of reactivity, the trifunctional siloxane unit is preferred. The molecular structure of the component (B) is exemplified by straight chain, cyclic, network and straight chain having partially branched. In addition, the viscosity is preferably such that the hydrosilylation reaction crosslinkable silicone composition can be dispersed in water. Specifically, the viscosity is preferably in the range of 1 to 10,000 mPa·s at 25° C.

Regarding the ratio of the components (A) and (B) in the composition, the molar ratio of the content of the alkenyl group (Alk) in the component (A) to the content of the hydrogen atom (H) connected to the silicon atom in the component (B) is:

$$H/Alk=0.7 \text{ to } 1.2$$

By reacting (A) and (B) within the ratio, silicone particles of the present invention can be prepared. Regarding the molar ratio of H:Alk, the preferable lower limit is H/Alk=0.8 or more, more preferably 0.85 or more, 0.90 or more, 0.95 or more, and 1.0 or more. If the ratio is lower than the lower limit, the alkenyl group remains. The preferably upper limit of the silicone particle powder is 1.15 or less, more preferably 1.10 or less, 1.05 or less, and 1.00 or less. If the ratio is higher than the upper limit, the unreacted hydrogen atom connected to the silicon atom tends to remain after the reaction. On the other hand, if the molar ratio is lower than the lower limit, the unreacted alkenyl group tends to remain after the reaction. By leaving these unreacted substances, silicone particles are aggregated and absorbed oil remains in the particles, and then the properties of the article obtained by using the silicone particles may be adversely affected. When the above alkenyl group is a hexenyl group and H/Alk is 0.9 to 1.1, particularly close to 1.0, the aggregation of silicone particles over time is most effectively inhibited.

The powder particle size is a measurement of silicone particles which are in the form of powder after drying. The powder particle size is measured by the median diameter (corresponding to 50% cumulative distribution of silicone particles, D50) of silicone particles, as identified by a laser diffraction type particle size distribution measuring device using a dispersion medium such as ethanol. The silicone particles according to the present invention are in the form of secondary particles obtained by aggregating a plurality of primary particles of silicone particles. The powder particle size is obtained by directly measuring the secondary particle size of silicone particles.

The powder particle size of silicone particles according to the present invention depends on the particle size of primary particles as the component of powder particles. Preferred range of the powder particle size is from 0.5 to 50 µm. The lower limit of this suitable range is preferably 1 µm, and more preferably 2 µm and 3 µm. Also, the upper limit of this suitable range is preferably 45 µm, more preferably 40 µm, 35 µm, 30 µm, 25 µm and 20 µm. If the size is smaller than the range, the crosslinking reaction hardly progresses, the particles tend to adhere to other particles, and then only the aggregated crosslinked product can be obtained. If the size is larger than the range, the compounding properties as particles in cosmetic materials and paints are impaired, and the feeling in use is poor.

On the other hand, silicone particles according to the present invention are primary particles before aggregation in a water dispersed form during the production. The particle size thereof is preferably 1 to 10 µm. If the primary particle size is lower than the lower limit, the crosslinking reactivity is poor. If the size is larger than the upper limit, the feeling in use and the compounding stability are impaired.

The hardness of silicone particles is preferably in the range of 5 to 70, as measured by a JIS A hardness meter specified in JIS K 6301 when silicone particle composition is cured into a sheet form. The hardness is more preferably 60 or less, and further preferably 50 or less. In particular, when the rubber hardness is within the above range, the resulting silicone particles are sufficiently suppressed in aggregation properties, and tend to have improved flowability, dispersibility, feeling of smoothness, and soft touch.

The silicone particles of the present invention are silicone particles in which the content of the hydrogen connected to the silicon atom per unit mass is 300 ppm or less, and the silicon atom in the siloxane as a component for silicone particles is crosslinked with the other silicon atom via an alkylene group having a carbon number of 4 to 20 (the first embodiment as described above); or silicone particles obtained by the crosslinking reaction of (A) an organopolysiloxane having two or more alkenyl groups having 4 or more and 20 or less carbon atoms in one molecule and (B) a specified organohydrogenpolysiloxane (the second embodiment as described above). From the viewpoint of inhibiting the aggregation of silicone particles, the relationship between the JIS-A hardness (Vα) of silicone particles and the powder particle size (Vβ) is preferably satisfies the following relationship.

$$V\alpha \times V\beta \leq 1{,}200$$

For silicone particles according to the above embodiments of the present invention, when the hardness and the particle size satisfy the above relationship, the aggregation of silicone particles is effectively inhibited. If the embodiments of the present invention described above are not satisfied, even if the hardness and the particle diameter satisfy the above relationship, the aggregation of silicone particles is not necessarily inhibited.

By emulsifying and curing the crosslinkable composition for forming silicone particles, the particle diameter of silicone particles can be easily adjusted. Examples of the emulsification include a method using a surfactant, an emulsification method using a mechanical shearing method using a mixing apparatus such as a stirring apparatus and an ultrasonic vibration machine, and the like. In this case, it is preferable to cool the curable silicone composition in advance before curing the aqueous dispersion of the crosslinkable composition for forming silicone particles to control its curability. When a surfactant is used, examples of the surfactant include nonionic, anionic, cationic and betaine type surfactants. The particle size of the resulting silicone particles varies depending on the type and content of the surfactant. In order to prepare silicone particles having smaller particle size, the addition amount of the surfactant is preferably in the range of 0.5 to 50 parts by mass based on 100 parts by mass of the crosslinkable composition for forming silicone particles. On the other hand, in order to prepare silicone particles having larger particle size, the addition amount of the surfactant is preferably in the range of 0.1 to 10 parts by mass based on 100 parts by mass of the crosslinkable composition for forming silicone particles. The addition amount of water as the dispersion medium is preferably in the range of 20 to 1,500 parts by mass, or 50 to 1,000 parts by mass based on 100 parts by mass of the crosslinkable composition for forming silicone particles. Since these surfactants are blended in the cosmetic as they are, silicone particles according to the present invention can be used as the cosmetic raw material.

In addition, it is preferable to use an emulsifier for uniformly dispersing the crosslinkable composition for forming silicone particles. Examples of the emulsifier include a homomixer, a paddle mixer, a Henschel mixer, a homodisper, a colloid mill, a propeller stirrer, a homogenizer, an inline continuous emulsifier, an ultrasonic emulsifier, and a vacuum kneader.

The aqueous dispersion of silicone particles can be prepared by standing the aqueous dispersion containing the crosslinkable composition for forming silicone particles as prepared by the above method at high temperature or at room temperature, and curing the crosslinkable composition for forming silicone particles in the aqueous dispersion. When heating the aqueous dispersion of the crosslinkable composition for forming silicone particles, the heating temperature is preferably 100° C. or less, and particularly preferably 10 to 95° C. Examples of a method of heating the aqueous dispersion of the crosslinkable composition for forming silicone particles include a method of directly heating the aqueous dispersion and a method of adding the aqueous dispersion into hot water. Silicone particles can then be prepared by removing water from the aqueous dispersion of silicone particles. Examples of the method of removing water include a method of drying by using a vacuum dryer, a hot air circulation type oven, or a spray dryer. The crosslinkable composition for forming silicone particles is cured to form silicone particles by standing at room temperature or by heating.

It is preferable to use an aqueous surfactant solution in order to stabilize the crosslinkable composition for forming silicone particles in the form of particles in the aqueous dispersion. The addition amount of the surfactant is preferably from 0.1 to 20 parts by mass, more preferably from 0.2 to 10 parts by mass, and particularly preferably from 0.2 to 5 parts by mass, based on 100 parts by mass of the crosslinkable composition for forming silicone particles. The addition amount of water is preferably from 40 to 2,000 parts by mass, and particularly preferably from 40 to 1,000 parts by mass, based on 100 parts by mass of the crosslinkable composition for forming silicone particles. The reasons are as follows. If the addition amount of water is less than 40 parts by mass based on 100 parts by mass of the crosslinkable composition for forming silicone particles, the uniform aqueous dispersion of the crosslinkable composition for forming silicone particles is hardly formed. If the addition amount is more than 2,000 parts by mass, the productivity of silicone particles is remarkably deteriorated.

On the other hand, in the step of removing water by the above method, it is known to methylate the remained hydrogen group connected to the silicon atom at the surface of silicone particles by a heating step, as a conventional technique. However, it is known that an unreacted hydrogen group connected to the silicon atom in silicone particles remains even after such a heating step. Although not bound by theory, it is believed that even if all the hydrogen group connected to the silicon atom at the surface of silicone particles, the hydrogen group connected to the silicon atom remains inside the particles, and the hydrogen group effects on the powder particle size of silicone particles over time. For this reason, depending on the prior art, it is impossible to obtain silicone particles in which the amount of hydrogen connected to the silicon atom is suppressed as low as the present invention.

The content of the hydrogen group connected to the silicon atom in silicone particles is not decreased even if a method of pulverizing the resulting silicone particles obtained by curing the crosslinkable composition for forming silicone particles by a pulverizer such as a grinder, or curing the particles by a vacuum dryer, a hot air circulation oven, or curing by spraying the particles with a sprayer such as a spray dryer in a hot air is performed.

Since the water-based dispersion of crosslinkable composition for forming silicone particles is easy to stabilize, the water to be used has little metal ion or halogen ion, and the electrical conductivity is preferably 1 µS/cm or less. Particularly preferred is an ion-exchanged water having an electrical conductivity of 0.5 µS/cm or less.

By obtaining fine particles of the mixture of the component (A) and the component (B) to prepare a water dispersible liquid, and then adding the catalyst for hydrosilylation reaction as the component (C) to obtain a crosslinkable composition for forming silicone particles, workability is improved, and it is hard for fine particles in the aqueous dispersion to aggregate.

The aqueous dispersion of silicone particles can be prepared by standing the aqueous dispersion of the crosslinkable composition for forming silicone particles as prepared by the above method at high temperature or at room temperature, and curing the crosslinkable composition for forming silicone particles in the aqueous dispersion.

When heating the aqueous dispersion of the crosslinkable composition for forming silicone particles, the heating temperature is preferably 100° C. or less, and particularly preferably 10 to 95° C. Examples of a method of heating the aqueous dispersion of the crosslinkable composition for forming silicone particles include a method of directly heating the aqueous dispersion and a method of adding the aqueous dispersion into hot water.

As the curing reaction for preparing silicone particles, the hydrosilylation reaction catalyst (C) component can be used. It is a catalyst that promotes curing of the crosslinkable composition for forming silicone particles, and is preferably a platinum group metal (group VIII of the periodic table) or a compound thereof. Preferred examples include platinum and/or platinum compounds such as finely divided platinum; solutions of chloroplatinic acid or chloroplatinic acid in alcohol; composites of chloroplatinic acid and alkenylsiloxanes; composites of platinum-diketones; platinum-alkenylsiloxane complexes; platinum-olefins complexes; platinum on silica, alumina, and similar carriers; or thermoplastic resins comprising platinum compounds. As other platinum group metal catalysts, rhodium, ruthenium, iridium or a palladium compound is exemplified. In addition, in order to carry out the hydrosilylation reaction, it is also possible to use hydrogen peroxide in water as the catalyst. Furthermore, a non-platinum-based hydrosilylation catalyst such as iron or iron/cobalt may be used.

Silicone particles are not particularly limited in shape and properties, and may be elastomer (rubber) particles, resin (resin) particles, or composite silicone particles of the same kind or different kinds. As silicone particles of the present invention, silicone elastomer particles having elasticity are more preferable. Silicone elastomer particles are used as cosmetic materials, coating agents, and the like as a feel improver. Silicone resin particles and silicone elastomer particles coated with silicone resin or silica fine particles are less agglomerated but have a hard texture, and may not have a soft touch such as in silicone elastomer particles in some cases.

The silicone particles of the present invention may be surface-treated if necessary. Typically, the particles are silica-coated, which may further improve the aggregation suppressing effect of silicone particles of the present invention. Further, other known hydrophilic treatment agents, hydrophobic treatment agents or the like may be used for surface treatment.

The silicone particles of the present invention may be in the form of dried powder particles or may be in the form of a water-based suspension dispersed in a hydrophilic dispersion medium such as water, alcohol or polyhydric alcohol. It may be in the form of an oily silicone particles composition dispersed or swollen in an oil agent.

The cosmetic material of the present invention will be described in detail.

This cosmetic material is characterized by containing the above-mentioned silicone particle. Examples of the cosmetic material include cleansing cosmetic material such as soaps, body shampoos, and facial cleansing creams; basic cosmetic material such as cosmetic lotion, cream/milky lotion, and pack; base makeup cosmetic material such as a face powder and foundation; eye cosmetic material such as lipstick, blusher, eye shadow, eyeliner and mascara; makeup cosmetic material such as manicure; hair cosmetic material such as shampoo, hair rinse, hair conditioner, hair growth agent, hair tonic and hair dye; aromatic cosmetic material such as perfume and eau de cologne; toothpaste; bath agent; and special cosmetic material such as depilatory agent, shaving lotion, antiperspirant/deodorant, and sunscreen agent. Examples of the dosage form of the cosmetic material include aqueous liquid, oily liquid, emulsion, cream, foam, semi-solid, solid and powder. This cosmetic material can also be used by spraying.

In this cosmetic material, the content of silicone particles is preferably in the range of 0.5 to 99.0% by mass, and particularly preferably in the range of 1.0 to 95% by mass in the cosmetic material. This is because, when the content of silicone particles exceeds the upper limit of the above range, the effect as a cosmetic material is lost, and if it is less than the lower limit of the above range, the feeling of use of the cosmetic material and the like are difficult to improve.

As a cosmetic raw material, it is also possible to disperse silicone particles in an aqueous phase or an oil phase using the cosmetic component described in the following paragraphs as a medium (aqueous medium or oil medium). Examples of the aqueous medium include water such as pure water, ion exchanged water, alkaline ion water, deep sea water, wave water, and natural water; and an aqueous medium being miscible with water, for example, lower alcohols such as ethyl alcohol, propyl alcohol and isopropyl alcohol; and polyhydric alcohols such as glycerin, 1,3 butylene glycol, isoprene glycol, and dipropylene glycol.

Examples of the oily medium (oil agent) include silicone oil, hydrocarbon oil, higher fatty acid, higher alcohol, ester oil (including fat and oil), ether oil, mineral oil, fluorine oil and the like. Among them, silicone oil, hydrocarbon oil, ester oil is more preferable from the viewpoint of feeling of use. Specific examples thereof include silicone oils such as dimethyl polysiloxane, methyl hydrogen polysiloxane, methyl phenyl polysiloxane, polyether modified organopolysiloxane, fluoroalkyl/polyoxyalkylene co-modified organopolysiloxane, alkyl modified organopolysiloxane, terminal modified organopolysiloxane, fluorine modified organopolysiloxane, amodimethicone, amino modified organopolysiloxane, acrylic silicone, and trimethylsiloxysilicic acid; hydrocarbon oils such as liquid paraffin, vaseline and squalane; and ester oils such as myristyl myristate, hexyl laurate, decyl oleate, isopropyl myristate, hexyldecyl dimethyl octanoate, glyceryl monostearate, diethyl phthalate, ethylene glycol monostearate, octyl oxystearate, isononyl isononanoate, and isotridecyl isononanoate. One or more of these oil agents can be used. Further, the content of the oil agent based on the total amount of the water-in-oil type emulsified cosmetic material used in the present invention is preferably from 10 to 50% by mass, and more preferably from 20 to 40% by mass, from the viewpoint of feeling in use and the storage stability.

The cosmetic material of the present invention may contain components commonly used in cosmetic materials, water, coloring agents, alcohols, water-soluble polymers, film forming agents, oil agents, oil-soluble gelling agents, organic modified clay mineral, surfactant, resin, salts, humectant, antiseptic, antimicrobial agent, antioxidant, pH adjuster, chelating agent, refreshing agent, anti-inflammatory agent, component for skin beauty (whitening agent, cell activation additives, agents for improving skin roughness, blood circulation promoters, skin astringents, antiseborrheic agents), vitamins, amino acids, nucleic acids, hormones, clathrate compounds, physiologically active substances, medicinal active ingredients, and perfumes, and these are not particularly limited. The content of each of components of the cosmetic material is, excluding water, preferably in the range of 0.5 to 99.0% by mass, and particularly preferably in the range of 1.0 to 95% by mass in the cosmetic material. When the content of one component of the cosmetic material exceeds the upper limit of the above range, the feeling in use as the cosmetic material is not preferable. In addition, when it is added, if the content is less than the lower limit of the above range, it will be difficult to obtain effects such as improvement in feeling of use in the cosmetic material. In addition, as for cosmetic components and blending amounts thereof, those disclosed in Japanese Unexamined Patent Publication No. 2015-113303 are incorporated herein by reference.

Water does not contain any harmful components to the human body and just needs to be clean, and examples thereof include tap water, purified water, mineral water, and deep sea water. In the case where the cosmetic material of the present invention is of an aqueous base, an optional water-soluble additive component can be blended in the water phase as long as the effect of the present invention is not impaired. In addition, for the purpose of improving the storage stability and the like of the cosmetic material, well-known pH adjusting agents, preservatives, antimicrobial agents or antioxidants can be added as appropriate.

Examples of the colorant include inorganic red pigments such as red iron oxide, iron oxide, iron hydroxide and iron titanate, inorganic brown pigments such as γ-iron oxide, inorganic yellow pigments such as yellow iron oxide and ocher, inorganic black pigments such as black iron oxide and carbon black, inorganic purple pigments such as manganese violet and cobalt violet, inorganic green pigments such as chromium hydroxide, chromium oxide, cobalt oxide and cobalt titanate, inorganic blue pigments such as Prussian blue and ultramarine blue, lake colorants of tar-based pigments of Red No. 3, Red No. 104, Red No. 106, Red No. 201, Red No. 202, Red No. 204, Red No. 205, Red No. 220, Red No. 226, Red No. 227, Red No. 228, Red No. 230, Red 401 No. 505, yellow No. 4, yellow No. 5, yellow No. 202, yellow No. 203, yellow No. 204, yellow No. 401, blue No. 1, blue No. 2, blue No. 201, blue No. 404, green No. 3, Green No. 201, Green No. 204, Green No. 205, Orange No. 201, Orange No. 203, Orange No. 204, Orange No. 206 and Orange No. 207 and the like, lake coloring pigments of natural pigments such as carminic acid, laccaic acid, carthamin, brasiline, and crocin; pearl pigments such as titanium oxide-coated mica, titanium mica, iron oxide treated mica titanium, titanium oxide coated mica, bismuth oxychloride, titanium oxide coated bismuth oxychloride, titanium oxide coated talc, fish scale foil and titanium oxide coated colored mica; and metal powder of aluminum, gold, silver, copper, platinum, stainless steel and the like.

It is preferable that these colorants are subjected to a water repellent treatment. Complexes of these coloring agents or those obtained by surface treatment with general oil, silicone compound, fluorine compound, surfactant or the like can also be used, and one or two or more thereof can be used.

An example of such a water repellent treatment is one in which a colorant is treated with various water repellent surface treatment agents, and examples thereof include organosiloxane treatment such as methyl hydrogen polysiloxane treatment, silicone resin treatment, silicone gum treatment, acrylic silicone treatment, and fluorinated silicone treatment, metal soap treatment such as zinc stearate treatment, silane treatment such as silane coupling agent treatment and alkylsilane treatment, perfluoroalkylsilane, perfluoroalkylphosphoric acid ester salt, and fluorine compound treatment such as perfluoropolyether treatment and amino acid treatment such as N-lauroyl-L-lysine treatment, oil treatment such as squalane treatment, acrylic treatment such as alkyl acrylate treatment, etc., and one or more of these can be used in combination.

As the alcohols, one or more selected from lower alcohols, sugar alcohols and higher alcohols can be used. Specific examples include lower alcohols such as ethanol and isopropanol; sugar alcohols such as sorbitol and maltose; and higher alcohols such as lauryl alcohol, myristyl alcohol, palmityl alcohol, stearyl alcohol, behenyl alcohol, hexadecyl alcohol, oleyl alcohol, isostearyl alcohol, hexyl dodecanol, octyldodecanol, cetostearyl alcohol, 2-decyltetradecinol, cholesterol, sitosterol, phytosterol, lanosterol, POE cholesterol ether, monostearyl glycerin ether (batyl alcohol), and monooleyl glyceryl ether (selachyl alcohol).

The water-soluble polymer is blended for the purpose of improving the feeling of use of the cosmetic material and may be amphoteric, cationic, anionic, nonionic, or water-swellable clay mineral as long as it is used in ordinary cosmetic materials, and one type or two or more types of water-soluble polymers can be used in combination. These water-soluble polymers have a thickening effect on water-containing components, and are therefore particularly useful when obtaining a gel-like water-containing cosmetic material, a water-in-oil emulsion cosmetic material, or an oil-in-water emulsion cosmetic material.

Examples of amphoteric water-soluble polymers include amphoteric starch, dimethyldiallylammonium chloride derivatives (for example, acrylamide/acrylic acid/dimethyldiallylammonium chloride copolymer, acrylic acid/dimethyldiallylammonium chloride copolymer), and methacrylic acid derivatives (for example, polymethacryloyl ethyl dimethyl betaine, N-methacryloyloxyethyl N, N-dimethyl ammonium-α-methyl carboxy betaine, alkyl methacrylate copolymer, etc.).

Examples of the cationic water-soluble polymers include quaternary nitrogen-modified polysaccharides (for example, cation modified cellulose, cation modified hydroxyethyl cellulose, cation modified guar gum, cation modified locust bean gum, cation modified starch and the like), dimethyl diallyl ammonium chloride derivative (for example, dimethyldiallylammonium chloride-acrylamide copolymer, polyethyldimethylmethylene chloride piperidinium etc.), vinylpyrrolidone derivatives (for example, vinylpyrrolidone-dimethylaminoethyl methacrylic acid copolymer salt, vinylpyrrolidone-methacrylamidopropyltrimethylammonium chloride copolymers, vinylpyrrolidone-methylvinylimidazolium chloride copolymer, etc.), and methacrylic acid derivatives (e.g., methacryloylethyldimethylvetainchloride methacryloylethyl trimethyl ammonium 2-hydroxyethyl methacrylate copolymer, methacryloyl ethyl dimethyl betaine chloride methacryloyloxyethyl trimethyl ammonium-methacrylate methoxy polyethylene glycol copolymer) and the like.

Examples of the anionic water-soluble polymer include polyacrylic acid or an alkali metal salt thereof, polymethacrylic acid or an alkali metal salt thereof, hyaluronic acid or an alkali metal salt thereof, acetylated hyaluronic acid or an alkali metal salt thereof, and a water-soluble polymer of an aliphatic carboxylic acid such as a hydrolyzate of a methyl vinyl ether-maleic anhydride copolymer or a metal salt thereof, carboxymethyl cellulose or an alkali metal salt thereof, a methyl vinyl ether-maleic half ester copolymer, an acrylic resin alkanol amine solution, and carboxyvinyl polymers.

Examples of the nonionic water-soluble polymers include natural polymer compounds such as polyvinylpyrrolidone, highly polymerized polyethylene glycol, vinylpyrrolidone/vinyl acetate copolymer, vinylpyrrolidone/dimethylaminoethyl methacrylate copolymer, vinylcaprolactam/vinylpyrrolidone/dimethylaminoethyl methacrylate copolymer, cellulose or derivatives thereof (e.g., methylcellulose, ethylcellulose, hydroxyethylcellulose, hydroxypropylcellulose, carboxymethylcellulose), keratin and collagen or derivatives thereof, calcium alginate, pullulan, agar, gelatin, tamarind seed polysaccharide, xanthan gum, carrageenan, high methoxyl pectin, low methoxyl pectin, guar gum, pectin, gum arabic, crystalline cellulose, arabinogalactan, karaya gum, tragacanth gum, alginic acid, albumin, casein, curdlan, duran gum, dextran, quince seed gum, tragacanth gum, chitin/chitosan derivatives, starch (rice, corn, potato, wheat, etc.), keratin and collagen or its derivatives.

The water-swellable clay mineral is an inorganic water-soluble polymer, which is a kind of a colloid-containing aluminum silicate having a three-layer structure and is generally represented by the formula:

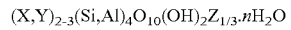

$$(X,Y)_{2-3}(Si,Al)_4O_{10}(OH)_2Z_{1/3} \cdot nH_2O$$

(where X is Al, Fe(III), Mn(III) or Cr(III), Y is Mg, Fe(II), Ni, Zn, or Li, Z is K, Na, or Ca).

Specific examples of such inorganic water-soluble polymers are bentonite, montmorillonite, paidelite, nontronite, saponite, hectorite, magnesium aluminum silicate, and silicic anhydride, which may be either natural products or synthetic products.

As the oil agent, any one of solid, semi-solid and liquid can be used. Specifically, one kind or two or more kinds selected from silicone oil, hydrocarbon oil, ester oil, vegetable fats and oils, animal fats and oils, fatty acids, higher alcohols, triglycerides, artificial sebum, and fluorine-based oils can be used.

Examples of the silicone oil include a cyclic organopolysiloxane such as hexamethylcyclotrisiloxane (D3), octamethylcyclotetrasiloxane (D4), decamethylcyclopentasiloxane (D5), dodecamethylcyclohexasiloxane (D6), 1,1-diethyl hexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethyl cyclotetrasiloxane, 1,3,5,7-tetracyclohexyltetramethylcyclotetrasiloxane, tris (3,3,3-trifluoropropyl) trimethylcyclotrisiloxane, 1,3,5,7-tetra (3-methacryloxypropyl) tetramethylcyclotetrasiloxane, 1,3,5,7-tetra (3-acryloxypropyl) tetramethylcyclotetrasiloxane, 1,3,5,7-tetra (3-carboxypropyl) tetramethylcyclotetrasiloxane, 1,3,5,7-tetra (3-vinyloxypropyl) tetramethylcyclotetrasiloxane, 1,3,5,7-tetra (p-vinylphenyl) tetramethylcyclotetrasiloxane, 1,3,5,7-tetra [3-(p-vinylphenyl) propyl] tetramethylcyclotetrasiloxane, 1,3,5,7-tetra (N-acryloyl-N-methyl-3-aminopropyl) tetramethylcyclotetrasiloxane, and 1,3,5,7-tetra (N, N-bis (lauroyl)-3-aminopropyl) tetramethylcyclotetrasiloxane. Examples of linear organopolysiloxane include dimethylpolysiloxane capped at both molecular chain terminals with trimethylsiloxy groups (low viscosity such as 2 cst or 6 cst or the like with a high viscosity of 1,000,000 cst, highly viscous dimethyl silicone), organohydrogen polysiloxane, trimethyl Siloxyl group-capped methylphenyl polysiloxane, dimethylsiloxane-methylphenylsiloxane copolymer capped at both molecular terminals with trimethylsiloxy groups, diphenylpolysiloxane capped at both molecular terminals with trimethylsiloxy groups, dimethylsiloxane capped at both molecular terminals with trimethylsiloxy groups • diphenyl Siloxane copolymer, trimethylpentaphenyltrisiloxane, phenyl (trimethylsiloxy) siloxane, methylalkyl polysiloxane capped at both molecular terminals with trimethylsiloxy groups, trimethylsiloxane at both molecular chain terminals A blocked dimethylpolysiloxane-methylalkylsiloxane copolymer, dimethylsiloxane capped at both molecular terminals with trimethylsiloxy groups, methyl (3,3,3-trifluoropropyl) siloxane copolymer, α, ω-dihydroxypolydimethylsiloxane, α, ω-diethoxypolydimethylsiloxane, 1,1,1,3,5,5,5-heptamethyl-3-octyltrisiloxane, 1,1,1,3,5,5,5-heptamethyl-3-Dodecyltrisiloxane, 1,1,1,3,5,5,5-heptamethyl-3-hexadecyl-trisiloxane, tristrimethylsiloxymethylsilane, tristrimethylsiloxyalkylsilane, tetrakistrimethylsiloxysilane, tetramethyl-1,3-Dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy-modified silicone, and higher fatty acid-modified silicone.

Examples of hydrocarbon oils include liquid paraffin, light liquid isoparaffin, heavy liquid isoparaffin, petrolatum, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene.polypropylene wax, squalane, squalene, pristane, and polyisoprene.

Examples of ester oil include hexyldecyl octanoate, cetyl octanoate, isopropyl myristate, isopropyl palmitate, butyl stearate, hexyl laurate, myristyl myristate, oleyl oleate, decyl oleate, octyl dodecyl myristate, octyl dodecyl myristate, hexyldecyl dimethyl octanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri 2-ethylhexanoate, trimethylolpropane tri-2-ethylhexanoate, ditrimethylolpropane triethylhexanoate, (isostearic acid/sebacic acid) ditrimethylolpropane, trimethylolpropane trioctanoate, trimethylolpropane triisostearate, diisopropyl adipate, diisobutyl adipate, 2-hexyldecyl adipate, di-2-heptylundecyl adipate, diisostearyl malate, monoisostearic acid hydrogenated castor oil, monoisostearic acid N-alkyl glycol, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl g urn ester, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyl octyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, N-lauroyl L-glutamic acid 2-octyldodecyl ester, N-lauroyl-L-glutamic acid di (cholesteryl/behenyl/octyldodecyl), N-lauroyl-L-glutamic acid di (cholesteryl/octyldodecyl), N-lauroyl-L-glutamic acid di (phytosteryl/behenyl/octyldodecyl), N-lauroyl-L-glutamic acid di (phytosteryl/octyldodecyl), N-lauroylsarcosine isopropyl, diisostearyl malate, neopentyl glycol dioctanoate, neopentanoic acid Isodecyl neopentanoate, isotridecyl neopentanoate, isostearyl neopentanoate, isononyl isononanoate, isotridecyl isononanoate, octyl isononanoate, isotridecyl isononanoate, diethyl pentane diol dineopentanoate, methyl pentane diene dineopentanoate, octyl dodecyl neodecanoate, 2-butyl dioctanoate-2-ethyl-1,3-propanediol, pentaerythrityl tetraoctanoate, hydrogenated rosin pentaerythrityl, pentaerythrityl triethylhexanoate, (palmitic acid/stearic acid/rosin acid) dipentaerythrityl, polyglyceryl tetraisostearate, polyglyceryl nonanaisostearate-10, deca (erucic acid/isostearic acid/ricinoleic acid) polyglyceryl-8, (hexyldecanoic acid/sebacic acid) diglyceryl oligoester, glycol distearate (ethylene glycol distearate), diisopropyl dimer linoleate, diisostearyl dimer linoleate, di (isostearyl/phytosteryl) dimer dilaurate, dimer linoleic acid (phytosteryl/behenyl) die margined linoleic acid, (phytosteryl/isostearyl/cetyl/stearyl/behenyl), dimer linoleic acid dimer linoleyl, diisostearic acid dimer linoleyl, dimer linoleyl hydrogenated rosin condensate, dimer rino rale hydrogenated rosin condensate, dimer linoleic acid hydrogenated castor oil, hydroxyalkyl dimer linoleyl ether, glyceryl triisooctanoate, glyceryl triisostearate, glyceryl trimyristate, glyceryl triisopalmitate, trioctanoic acid glyceryl trioleate, glyceryl trioleate, glyceryl diisostearate, glyceryl tri (caprylic/capric) acid, glyceryl tri (caprylic/capric acid/myristic acid/stearic acid), hydrogenated rosin triglyceride (hydrogenated ester gum), rosin triglyceride (ester gum), glyceryl eicosane behenate, glyceryl di-2-heptylundecanoate, diglyceryl myristate isostearate, cholesteryl acetate, cholesteryl nonanoate, cholesteryl phosphate, cholesteryl isostearate, cholesteryl oleate, cholesteryl 12-hydroxystearate, macadamia nut oil fatty acid cholesteryl, macadamia nut oil fatty acid phytosteryl, phytosteryl isostearate, cholesteryl soft lanolin fatty acid cholesteryl, hard lanolin fatty acid cholesteryl, long chain branched fatty acid cholesteryl, long chain α-hydroxy fatty acid cholesteryl, octyl dodecyl ricinoleate, octyl dodecyl lanolin fatty acid, octyl dodecyl erucate, isostearic acid hydrogenated castor oil, avocado oil fatty acid ethyl, and lanolin fatty acid isopropyl.

Examples of natural animal and vegetable fats and oils and semi-synthetic fats and oils include avocado oil, linseed oil, almond oil, Ibota wax, eno oil, olive oil, cacao butter, kapok row, kaya oil, carnauba wax, liver oil, candelilla wax, beef tallow, beef tallow fat, sesame oil, cinnamon oil, jojobaro, olive oil, rice bran oil, sesame oil, rice germ oil, rice bran oil, sugarcane wax, sasanqua oil, safflower oil, shea butter, squalane, shellac wax, turtle oil, soybean oil, tea seed oil, camellia oil, evening primrose oil, corn oil, lard oil, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, additives jojoba ester, macadamia nut oil, beeswax, mink oil, cottonseed oil, cotton wax, Japanese wolf berry wolf berry kernel oil, montan wax, coconut oil, hardened coconut oil, tall oil fatty acid glyceride, sheep fat, peanut oil, lanolin, liquid lanolin, reduced lanolin, lanolin alcohol, hard lanolin, acetate lanolin, lanolin fatty acid isopropyl, POE lanolin alcohol ether, POE lanolin alcohol acetate, lanolin fatty acid polyethylene glycol, POE hydrogenated lanolin alcohol ether, egg yolk oil and the like. Here, POE means polyoxyethylene.

Examples of higher fatty acid includes lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA) Isostearic acid, and 12-hydroxystearic acid.

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradec norle, cholesterol, sitosterol, phytosterol, lanosterol, POE cholesterol ether, monostearyl glycerin ether (batyl alcohol), and monooleyl glyceryl ether (celkyl alcohol).

As the fluorine-based oil agent, perfluoropolyether, perfluorodecalin, perfluorooctane and the like can be mentioned, and one or more of these oil agents can be used as required.

Examples of the oil-soluble gelling agent include metallic soaps such as aluminum stearate, magnesium stearate and zinc myristate; amino acid derivatives such as N-lauroyl-L-glutamic acid and α, γ-di-n-butylamine; dextrin fatty acid esters such as dextrin palmitic acid esters, dextrin stearate esters, and dextrin 2-ethylhexanoic acid palmitate; sucrose fatty acid esters such as sucrose palmitate esters and sucrose stearate esters; ructooligosaccharide fatty acid esters such as inulin stearate and fructooligosaccharide 2-ethylhexanoic acid ester; benzylidene derivatives of sorbitol such as monobenzylidene sorbitol and dibenzylidenesorbitol; and clay minerals modified with organic compounds such as dimethylbenzyldodecylammonium montmorilonite clays and dimethyl dioctadecyl ammonium montmorillonite clays, and these may be used singly or two or more thereof may be used as needed.

As the surfactant, one or more selected from the group consisting of a silicone surfactant, an anionic surfactant, a cationic surfactant, a nonionic surfactant, an amphoteric surfactant, and a semipolar surfactant can be used in combination.

Silicone surfactants are often used as components for emulsification and washing of oil agents, dispersions of powder, and surface treatment, and typically include polyglyceryl-modified silicone, glyceryl-modified silicone, sugar-modified silicone, fluorine polyether-modified silicone, polyether-modified silicone, carboxylic acid-modified silicone, sugar-modified silicone, linear silicone-polyether block copolymer (polysilicone-13, etc.), and long chain alkyl/polyether co-modified silicone.

Examples of the anionic surfactant include saturated or unsaturated fatty acid salts (for example, sodium laurate, sodium stearate, sodium oleate, sodium linolenate and the like), alkyl sulfates, alkylbenzene sulfonic acids (for example, hexylbenzene sulfonic acid, octylbenzenesulfonic acid, dodecylbenzenesulfonic acid, etc.) and salts thereof, polyoxyalkylene alkyl ether sulfates, polyoxyalkylene alkenyl ether sulfates, polyoxyethylene alkyl sulfate, sulfosuccinic acid alkyl ester salts, polyoxyalkylene sulfosuccinic acid alkyl ester salts, polyoxyalkylene alkyl phenyl ether sulfates, alkanesulfonic acid salts, octyltrimethylammonium hydroxide, dodecyltrimethylammonium hydroxide, alkyl sulfonate, polyoxyethylene alkyl phenyl ether sulfate, polyoxyalkylene alkyl ether acetate, alkyl phosphate, polyoxyalkylene alkyl ether phosphate, acyl glutamate, α-acyl sulfonate, alkyl sulfonate, alkylallylsulfonate, α-olefin sulfonate, alkylnaphthalenesulfonate, alkanesulfonate, alkyl or alkenyl sulfate, alkylamide sulfate, alkyl or alkenyl phosphate, alkylamide phosphate, alkyloyl alkyl taurine salt, N-acyl amino acid salt, sulfosuccinate, alkyl ether carboxylate, amide ether carboxylate, α-sulfo fatty acid ester salt, alanine derivatives, glycine derivatives, and arginine derivatives. Examples of the salt include an alkali metal salt such as a sodium salt, an alkaline earth metal salt such as a magnesium salt, an alkanolamine salt such as a triethanolamine salt, and an ammonium salt.

Examples of the cationic surfactant include alkyltrimethylammonium chloride, stearyltrimethylammonium chloride, lauryltrimethylammonium chloride, cetyltrimethylammonium chloride, tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium chloride (2EO), benzalkonium chloride, alkylbenzalkonium chloride, alkyldimethylbenzalkonium chloride, benzethonium chloride, stearyl dimethyl benzyl ammonium chloride, lanolin-derived quaternary ammonium salt, diethylaminoethylamide stearate, dimethylaminopropylamide stearate, amidopropyldimethylhydroxypropylammonium chlorobehenate, stearoyl colaminoformylmethylpyridinium chloride, cetylpyridinium chloride, tall oil alkylbenzylhydroxyethylimidazolinium chloride, and benzylammonium salt.

Examples of the nonionic surfactant include polyglyceryl diisostearate, diglyceryl polyhydroxystearate, isostearyl glyceryl ether, polyoxyalkylene ethers, polyoxyalkylene alkyl ethers, polyoxyalkylene fatty acid esters, polyoxyalkylene fatty acid diesters, polyoxyalkylene (hardened) castor oil, polyoxyalkylene alkylphenol, polyoxyalkylene alkyl phenyl ether, polyoxyalkylene phenyl ether, polyoxyalkylene alkyl ester, polyoxyalkylene alkyl esters, sorbitan fatty acid esters, polyoxyalkylene sorbitan alkyl esters, polyoxyalkylene sorbitan fatty acid ester, polyoxyalkylene sorbit fatty acid ester, polyoxyalkylene glycerin fatty acid ester, polyglycerin alkyl ether, polyglycerin fatty acid ester, sucrose fatty acid ester, fatty acid alkanolamide, alkyl glucoside, polyoxyalkylene fatty acid bisphenyl ethers, polypropylene glycol, diethylene glycol, polyoxyethylene-polyoxypropylene block polymers, alkyl polyoxyethylene-polyoxypropylene block polymer ethers, polyoxyethylene-polyoxypropylene block polymers, alkyl polyoxyethylene-polyoxypropylene block polymer ether, and fluorine-based surfactant.

Examples of the amphoteric surfactant include imidazoline type, amidobetain type, alkylbetaine type, alkylamidobetain type, alkylsulfobetaine type, am idosulfobetaine type, hydroxysulfobetaine type, carbobetaine type, phosphobetaine type, aminocarboxylic acid type, and amide amino acid type amphoteric surfactants. Specific examples thereof include imidazoline type amphoteric surfactants such as 2-undecyl-N, N, N-(hydroxyethylcarboxymethyl)-2-imidazoline sodium and 2-cocoyl-2-imitazolinium hydroxide-1-carboxyethyloxy-2-sodium; alkylbetaine type amphoteric surfactants such as lauryldimethylaminoacetic acid betaine and myristyl betaine; amidobetaine type amphoteric surfactants such as coconut oil fatty acid amidopropyldimethylaminoacetic acid betaine, palm kernel oil fatty acid amidopropyldimethylaminoacetic acid betaine, beef tallow fatty acid amidopropyldimethylaminoacetic acid betaine, hydrogenated beef tallow fatty acid amidopropyldimethylaminoacetic acid betaine, lauric acid amidopropyldimethylaminoacetic acid betaine, myristic acid amidopropyldimethylaminoacetic acid betaine, palmitic acid amidopropyldimethylaminoacetic acid, stearic acid amidopropyldimethylaminoacetic acid betaine and oleic acid amidopropyldimethylaminoacetic acid betaine; alkylsulfobetaine type amphoteric surfactants such as coconut oil fatty acid dimethylsulfopropyl betaine; alkylhydroxysulfobetaine type amphoteric surfactants such as lauryl dimethylaminohydroxysulfobetaine; phosphobetaine type amphoteric surfactants such as lauryl hydroxyphosphobetaine; amide amino acid type amphoteric surfactants such as N-lauroyl-N'-hydroxyethyl-N'-carboxymethylethylenediamine sodium, N-oleoyl-N'-hydroxyethyl-N'-carboxymethylethylenediamine sodium, N-cocoyl-N'-hydroxyethyl-N'-carboxymethylethylenediamine sodium, N-lauroyl-N'-hydroxyethyl-N'-carboxymethylethylenediamine potassium, N-oleoyl-N'-hydroxyethyl-N'-carboxymethylethylenediamine potassium, N-lauroyl-N-hydroxyethyl-N'-carboxymethylethylenediamine sodium, N-oleoyl-N-hydroxyethyl-N'-carboxymethylethylenediamine sodium, N-cocoyl-N-hydroxyethyl-N'-dicarboxymethylethylenediamine sodium, N-lauroyl-N-hydroxyethyl-N'—N'-dicarboxymethylethylenediamine monosodium, N-oleoyl-N-hydroxyethyl-N'—N'-dicarboxymethylethylenediamine monosodium, N-cocoyl-N-hydroxyethyl-N'—N'-dicarboxymethylethylenediamine monosodium, N-lauroyl-N-hydroxyethyl-N'—N'-dicarboxymethylethylenediamine disodium, N-oleoyl-N-hydroxyethyl-N'—N'-dicarboxymethylethylenediamine disodium, and N-cocoyl-N-hydroxyethyl-N'—N'-dicarboxymethylethylenediamine disodium.

Examples of the semipolar surfactant include alkylamine oxide surfactants, alkylamine oxides, alkylamidoamine oxides, alkylhydroxyamine oxides, and the like. Of these, alkyldimethylamine oxides having 10 to 18 carbon atoms, alkoxyethyl dihydroxyethylamine oxides having 8 to 18 carbon atoms and the like are preferably used. Specific examples thereof include dodecyl dimethyl amine oxide, dimethyl octyl amine oxide, diethyl decyl amine oxide, bis-(2-hydroxyethyl) dodecyl amine oxide, dipropyl tetradecyl amine oxide, methylethyl hexadecyl amine oxide, dodecyl amidopropyl dimethyl amine oxide, cetyl dimethyl amine oxide, stearyl dimethyl amine oxide, tallow dimethyl amine oxide, dimethyl 2-hydroxyoctadecyl amine oxide, lauryl dimethyl amine oxide, myristyl dimethyl amine oxide, stearyl dimethyl amine oxide, isostearyl dimethyl amine oxide, palm fatty acid alkyldimethylamine oxide, caprylic acid amidopropyldimethylamine oxide, capric acid amidopropyldimethylamine oxide, lauric acid amidopropyldimethylamine oxide, myristic acid amidopropyldimethylamine oxide, palmitic acid amidopropyldimethylamine oxide, stearic acid amidopropyldimethylamine oxide, isostearic acid amidopropyldimethylamine oxide, oleic acid amidopropyldimethylamine oxide, ricinoleic acid amidopropyldimethylamine oxide, 12-hydroxystearic acid amidopropyldimethylamine oxide, coconut fatty acid amidopropyldimethylamine oxide, palm kernel oil fatty acid amidopropyldimethylamine oxide, castor oil fatty acid amidopropyl dimethyl amine oxide, lauric acid amidoethyldimethylamine oxide, myristic acid amidoethyldimethylamine oxide, coconut fatty acid amidoethyldimethylamine oxide, lauric acid amidoethyldiethylamine oxide, myristic acid amidoethyldiethylamine oxide, coconut fatty acid amidoethyldiethylamine oxide, lauric acid amidoethyldihydroxyethylamine oxide, myristic acid amidoethyl dihydroxy ethylamine oxide, and coconut fatty acid amide ethyl dihydroxyethylamine oxide.

Salts include inorganic salts, organic acid salts, amine salts and amino acid salts. Examples of the inorganic salt include sodium salts, potassium salt, magnesium salt, calcium salt, aluminum salt, zirconium salt, zinc salt and the like of an inorganic acid such as hydrochloric acid, sulfuric acid, carbonic acid and nitric acid; and examples of salts of organic acids include acetic acid, dehydroacetic acid, citric acid, malic acid, succinic acid, ascorbic acid and stearic acid; and amine salts and amino acid salts such as salts of amines such as triethanolamine and salts of amino acids such as glutamic acid. In addition, salts such as hyaluronic acid and chondroitin sulfate, aluminum zirconium glycine complex and the like, and acid-alkali neutralizing salts used in cosmetic formulations and the like can also be used.

Examples of the humectant include polyhydric alcohols such as glycerin, sorbitol, propylene glycol, propylene glycol, dipropylene glycol, 1,3-butylene glycol, glucose, xylitol, maltitol and polyethylene glycol; hyaluronic acid, chondroitin sulfate, pyrrolidone carboxylate, polyoxyethylene methyl glucoside, polyoxypropylene methyl glucoside, PEG/PPG dimethyl ether, and the like.

Examples of antiseptics include paraoxybenzoic acid alkyl ester, benzoic acid, sodium benzoate, sorbic acid, potassium sorbate, and phenoxyethanol, and examples of the antibacterial agent include benzoic acid, salicylic acid, carbolic acid, sorbic acid, paraoxybenzoic acid alkyl esters, parachloromethacresol, hexachlorophene, benzalkonium chloride, chlorhexidine chloride, trichlorocarbanilide, triclosan, photosensitizers, phenoxyethanol and the like, but in the case of lipstick, antiseptics are preferably not blended.

Examples of the antioxidant include tocopherol, butylhydroxyanisole, dibutylhydroxytoluene, phytic acid and the like.

Examples of the pH adjuster include lactic acid, citric acid, glycolic acid, succinic acid, tartaric acid, dl-malic acid, potassium carbonate, sodium bicarbonate, ammonium hydrogen carbonate, and the like.

Examples of the chelating agent include alanine, sodium edetate, sodium polyphosphate, sodium metaphosphate, and phosphoric acid.

Examples of a refreshing agent include L-menthol and camphor, and examples of anti-inflammatory agents include allantoin, glycyrhetinic acid, glycyrrhizic acid, tranexamic acid, azulene and the like.

Examples of skin-care ingredients include whitening agents such as placenta extracts, arbutin, glutathione and saxifrage extract, cell activators such as royal jelly, roughness improving agents, blood circulation promotion agents such as nonylic acid warenylamide, nicotinic acid benzyl ester, β-butoxyethyl nicotinate ester, capsaicin, zingerone, cantharis tincture, ichthamol, caffeine, tannic acid, α-borneol, tocopherol nicotinate, inositol hexanicotinate, cycllandelate, cinnarizine, tolazoline, acetylcholine, verapamil, cepharanthin, and γ-oryzanol, astringents such as zinc oxide and tannic acid, anti-seborrhoeic agents such as sulfur and thiantrol, and the like. Examples of vitamins include vitamin A such as vitamin A oil, retinol, retinol acetate, and retinol palmitate, vitamin B such as vitamin B2 such as riboflavin, riboflavin butyrate and flavin adenine nucleotide, vitamin B6 such as pyridoxine hydrochloride, pyridoxine dioctanoate, and pyridoxine tripalmitate, vitamin B12 and its derivatives, and vitamin B15 and its derivatives, vitamin C such as L-ascorbic acid, L-ascorbic acid dipalmitate, sodium L-ascorbic acid-2-sulfate, and L-ascorbic acid phosphate dipotassium, vitamin D such as ergocalciferol and cholecalciferol, vitamin E such as α-tocopherol, β-tocopherol, γ-tocopherol, dl-α-tocopherol acetate, dl-α-tocopherol nicotinate, and dl-α-tocopherol succinate, vitamin H, vitamin P, nicotinic acids such as nicotinic acid and benzyl nicotinic acid, and pantothenic acids such as calcium pantothenate, D-pantothenyl alcohol, pantothenyl ethyl ether, and acetyl pantothenyl ethyl ether.

Amino acids include amino acids and/or salts thereof such as glycine, valine, leucine, isoleucine, serine, threonine, phenylalanine, arginine, lysine, aspartic acid, glutamic acid, cystine, cysteine, methionine, and tryptophan.

Examples of the nucleic acid include deoxyribonucleic acid and the like, and examples of the hormone include estradiol and ethenylestradiol.

The physiologically active ingredient is a substance which gives some physiological activity to the skin or hair when it is applied to the skin or hair, and is lipophilic. For example, an anti-inflammatory agent, an antiaging agent, a tightening agent, a hair growth agent, a hair growth agent, a moisturizer, a blood circulation promoter, a desiccant, a warming sensation agent, vitamins, a wound healing accelerator, a stimulative reliever, an analgesic, a cell activator, an enzyme component and the like can be mentioned. Similarly, natural plant extract components, seaweed extract components, and/or crude drug ingredients can be preferably incorporated.

The pharmaceutical active ingredient is a substance having a disease therapeutic effect, and examples thereof include a protein, a peptide, and a low molecular weight compound.

The fragrance is not particularly limited as long as it is a lipophilic perfume, and may be a perfume extracted from flowers, seeds, leaves, roots or the like of various plants, a fragrance extracted from seaweeds, a fragrance extracted from various parts or secretions of animals (e.g., palm civet and Ambergris) and artificially synthesized fragrances (e.g., menthol, musk, acetate, and vanilla). Perfumes are compounded to impart fragrance and aroma to the cosmetic. Dyes include oil-soluble dyes, extender pigments, inorganic pigments, organic pigments, and lipophilic fluorescent brighteners and the like.

In order to produce the cosmetic of the present invention, it can be easily produced simply by uniformly mixing the cosmetic raw material of the present invention and other cosmetic raw materials as described above. As the mixing means, various mixing apparatus and kneading apparatus usually used for manufacturing cosmetics can be used. Examples of such devices include homomixers, paddle mixers, Henschel mixers, homodisper, colloid mixers, propeller stirrers, homogenizers, inline continuous emulsifiers, ultrasonic emulsifiers, and vacuum type kneaders.

Next, the paint according to one embodiment of the present invention will be described in detail.

The paint according to one embodiment of the present invention is characterized by containing the above-mentioned silicone particle. Examples of the coating material include a room temperature curing type, a room temperature drying type, and a heat curing type coating material, and examples thereof include aqueous, oily and powdery forms depending on their properties. Furthermore, polyurethane resin paint, butyral resin paint, long oil phthalic acid resin paint, alkyd resin paint, amino alkyd resin paint comprising amino resin and alkyd resin, epoxy resin paint, acrylic resin paint, phenolic resin paint, silicone modified epoxy resin paint, silicone modified polyester resin paint, silicone resin paints are exemplified depending on the resin of the vehicle.

In this paint, it is preferable that the above-mentioned silicone particles have affinity or reactivity with the resin in the paint. For example, in paints using epoxy resin as a vehicle, they are preferably silicone particles having epoxy group or amino group. In a coating material using a polyurethane resin or an amino resin as a vehicle, silicone particles having an amino group are preferable.

In this paint, the content of the above-mentioned silicone particles is not limited, but in order to impart uniform and soft matting property to the obtained coating film, it is preferably in the range of 0.1 to 150 parts by mass, more preferably in the range of 0.1 to 100 parts by mass, and particularly preferably in the range of 0.1 to 50 parts by mass, based on 100 parts by mass of the resin solid content.

In addition to the above-mentioned silicone particles, the paint may contain an alcohol such as methanol or ethanol, a ketone such as methyl ethyl ketone or methyl isobutyl ketone, an ester such as ethyl acetate, butyl acetate or cellosolve acetate, an amide such as N,N-dimethylformamide, an olefin such as hexane, heptane or octane; an organic solvent such as an aromatic hydrocarbon such as toluene or xylene; a thickener comprising a pigment or a polymer compound; a flame retardant; or a weathering resistance imparting agent.

By heating an aqueous dispersion of the crosslinkable composition for forming silicone particles or an aqueous dispersion of the crosslinkable composition for forming silicone particles prepared by adding the component (C) to the aqueous dispersion of the silicone composition except for the component (C) to room temperature, or 100° C. or less, preferably 70° C. or less, it is possible to promote the crosslinking of the crosslinkable composition for forming silicone particles dispersed in water.

Next, silicone particles can be recovered by removing water from the aqueous dispersion of silicone particles obtained by curing the crosslinkable composition for forming silicone particles dispersed in water. As a method for recovering silicone particles, a method by heating or depressurizing the aqueous dispersion of silicone particles or by hot air drying, air drying or the like is exemplified. In addition, it is possible to easily remove moisture by filtering this water dispersion before drying or subjecting this water dispersion to separation by centrifugation or salting out.

Since such a resin additive of the present invention can impart flexibility and thermal shock resistance to the resin, it is suitable as additives for thermosetting resins such as epoxy resin and phenol resin, or an additive for thermoplastic resins such as polyethylene resin, polypropylene resin, nylon resin, polyester resin and the like.

Next, the electronic material which is one embodiment of the present invention will be described in detail.

An electronic material according to one embodiment of the present invention contains the crosslinkable composition for forming silicone particles as described above. In the electronic material of one embodiment of the present invention, the content of the crosslinkable composition for forming silicone particles is not limited, but it is preferably in the range of 0.1 to 100 parts by weight based on 100 parts by weight of the curable resin. This is because if the content of the resin additive is less than the lower limit of the above range, flexibility and thermal shock resistance of the obtained cured resin are lowered, and in particular, thermal shock resistance after moisture absorption tends to decrease. On the other hand, if it exceeds the upper limit of the above range, the mechanical properties of the obtained cured resin tend to deteriorate.

In the electronic material which is one embodiment of the present invention, as a curable resin which is a main component thereof, phenol resin, formaldehyde resin, xylene resin, xylene-formaldehyde resin, ketone-formaldehyde resin, furan resin, urea resin, imide resin, melamine resin, alkyd resins, unsaturated polyester resins, aniline resins, sulfone-amide resins, silicone resins, epoxy resins, and copolymer resins of these resins can be mentioned, and two or more of these curable resins can also be used in combination. In particular, the cured resin is preferably at least one selected from the group consisting of epoxy resin, phenol resin, imide resin, and silicone resin. The epoxy resin may be a compound containing a glycidyl group or an alicyclic epoxy group, and examples thereof include an o-cresol novolak type epoxy resin, a biphenyl type epoxy resin, a bisphenol A type epoxy resin, a bisphenol F type epoxy resin, a dicyclo pentadiene type epoxy resin, a naphthalene type epoxy resin, an anthracene type epoxy resin, a naphthol aralkyl type epoxy resin, a polyvinyl phenol type epoxy resin, a diphenyl methane type epoxy resin, a diphenyl sulfone type epoxy resin, a triphenol alkane type epoxy resin, a cresol and naphthol condensation type epoxy resin, a bisphenylethylene type epoxy resin, a fluorene type epoxy resin, a stilbene type epoxy resin, a spirocumaron type epoxy resin, a norbornene type epoxy resin, terpene type epoxy resins, phenol cyclohexane type epoxy resins, halogenated epoxy resins, imide group-containing epoxy resins, maleimide group-containing epoxy resins, allyl group-modified epoxy resins, and silicone-modified epoxy resins. Also, as this phenolic resin, phenol resins such as polyvinyl phenol type, phenol novolac type, naphthol type, terpene type, phenol dicyclopentadiene type, phenol aralkyl type, naphthol aralkyl type, triphenol alkane type, dicyclopentadiene type, cresol/naphthol condensation type, and xylene/naphthol co-condensation type can be exemplified. As the silicone resin, an epoxy-modified silicone resin obtained by reacting an epoxy resin with a silanol group in a silicone resin or a silicon atom-bonded alkoxy group is exemplified. As a curing mechanism of such curable resin, high energy ray curable type such as thermosetting type, ultraviolet ray or radiation, moisture curing type, condensation reaction curing type and addition reaction curing type are exemplified. Further, the properties of such a curable resin at 25° C. are not limited, and may be either a liquid state or a solid state in which the curable resin is softened by heating.

In addition, as an optional component of the electronic material of one embodiment of the present invention, a curing agent, a curing accelerator, a filler, a photosensitizer, a higher fatty acid metal salt, an ester wax, a plasticizer and the like can be blended. Examples of the curing agent include organic acids such as carboxylic acid and sulfonic acid and anhydrides thereof; organic hydroxy compounds; organosilicon compounds having a silanol group, alkoxy group, or halogeno group; and primary or secondary amino compounds. Two or more of these can be combined. Examples of the curing accelerator include tertiary amine compounds, organometallic compounds such as aluminum and zirconium, organic phosphorus compounds such as phosphine, heterocyclic amine compounds, boron complex compounds, organic ammonium salts, organic sulfonium salts, organic peroxides, and hydrosilylation catalysts. Further, as this filler, fibrous fillers such as glass fiber, asbestos, alumina fiber, ceramic fiber containing alumina and silica as a component, boron fiber, zirconia fiber, silicon carbide fiber, metal fiber, polyester fiber, aramid fiber, nylon fiber, phenol fiber, and natural animal and plant fibers; and granular fillers such as fused silica, precipitated silica, fumed silica, calcined silica, zinc oxide, calcined clay, carbon black, glass beads, alumina, talc, calcium carbonate, clay, aluminum hydroxide, barium sulfate, titanium dioxide, aluminum nitride, silicon carbide, magnesium oxide, beryllium oxide, kaolin, mica, zirconia and the like can be exemplified, and two or more of these can be combined.

Furthermore, since silicone particles of the present invention are excellent in stress relaxation effect when compounded in a resin, they may be incorporated in epoxy resin or the like for a printed wiring board to form a prepreg. Furthermore, they can be formed into a copper foil with filler particle-containing resin layer for a printed wiring board having a resin layer containing silicone particles of the present invention on one surface of copper foil and used for copper clad laminate (CCL) applications.

EXAMPLES

Silicone particles of the present invention and the method for producing them will be explained in detail by Examples and Comparative Examples. However, the present invention is not limited to only these examples. The viscosity in the examples is a value at 25° C. The properties of silicone particles were measured as follows.

[JIS A Hardness of the Cured Silicone Particles]

The curable silicone composition, which is a raw material of the cured silicone particles, was heated in a heating oven at 150° C. for 1 hour to be cured into a sheet form. This hardness was measured with a JIS A hardness meter specified in JIS K 6253.

[SiH Residual Amount of the Cured Silicone Particles]

An equivalent solution of potassium hydroxide in ethanol at a concentration of 40% to the unit mass of the cured silicone particles was added, the mixture was left standing for 1 hour, the generated hydrogen gas until the reaction was completed was collected, the generation amount of hydrogen was measured by a headspace gas chromatography, and the residual amount (ppm) of the hydrogen connected to the silicon atom per unit mass was measured.

[Average Particle Diameter of Primary Particles]

The emulsion before adding the platinum catalyst was measured by a laser diffraction type particle size distribution analyzer (LS-230 by Beckman Coulter), and its median diameter (particle diameter corresponding to 50% of cumulative distribution, 50% particle diameter) was taken as the average particle diameter.

[Powder Particle Size]

Using ethanol as a dispersion medium, the particle diameter of the cured silicone particle was measured with a laser diffraction type particle size distribution measuring instrument (LA-500, manufactured by Horiba, Ltd.) and values of median diameter (particle size corresponding to 50% of the cumulative distribution, D90, μm) and arithmetic dispersion (showing a degree of dispersion of particle size distribution, SD, μm2) of the cured silicone particles in the ethanol were obtained. In the measurement sample, the cured silicone particles (1 g) and the ethanol (100 mL) were dispersed in a 300 mL cup using a stirring blade and an ultrasonic oscillator.

[Measurement Method of Mixture Viscosity]

Cured silicone particles (6 g) and decamethylcyclopentasiloxane (58 g) were weighed in a 300 mL cup and stirred for 2 minutes at 4000 rpm with a disper. Thereafter, using a BM type rotary viscometer (manufactured by Toki Sangyo Co., Ltd.) under a condition of 60 rpm with a rotor No. 2, a value after 1 minute was defined as viscosity.

[Measurement Method of Powder Oil Absorption Amount]

In a 100 ml beaker, 5 g of the cured silicone particles were placed, and while the cured silicone particles were gently stirred with a glass rod, squalane, cetyl ethylhexanoate (Note 1), mineral oil (Note 2), or decamethylcyclopentasiloxane (Note 3) was dropped drop by drop, and a dropping amount of oil required until the cured silicone particles and the oil became a uniform pasty substance was determined. The ratio of the dropping amount of the oil to the cured silicone particles was set as the oil absorption amount (weight %) of the organic crosslinked particles.

Note 1: CEH manufactured by KOKYU ALCOHOL KOGYO. CO., LTD.

Note 2: HICALL K-230 manufactured by KANEDA Co., Ltd.

Note 3: SH245 manufactured by Dow Corning Toray Co., Ltd.

The average formulae of the components (A) and (B) used in the Examples and Comparative Examples are listed below.

In the following formulae, Vi represents $CH_2=CH-$, Me represents $CH_3-$, and He represents $CH_2=CH-C_4H_8-$.

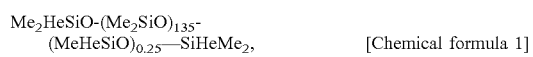

$Me_2HeSiO-(Me_2SiO)_{135}-$
$(MeHeSiO)_{0.25}-SiHeMe_2,$ [Chemical formula 1]

The alkenyl group content is 0.97 wt %. The viscosity is 420 mPa·s.

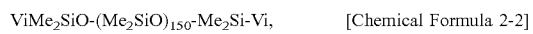

$ViMe_2SiO-(Me_2SiO)_{150}-Me_2Si-Vi,$ [Chemical Formula 2-2]

The alkenyl group content is 0.47 wt %. The viscosity is 360 mPa·s.

$ViMe_2SiO-(Me_2SiO)_{130}-$
$(ViMeSiO)_2-Me_2Si-Vi$ [Chemical Formula 3-3]

The alkenyl group content is 1.08 wt %. The viscosity is 370 mPa·s.

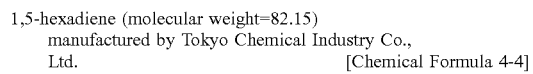

1,5-hexadiene (molecular weight=82.15)
manufactured by Tokyo Chemical Industry Co., Ltd. [Chemical Formula 4-4]

$Me_3SiO-(Me_2SiO)_{33.7}-$
$(HMeSiO)_{11.5}-SiMe_3,$ [Chemical Formula 2-1]

The content of the hydrogen bonded to the silicon atom is 0.44 wt %. The viscosity is 50 mPa·s.

$(Me_3SiO_{1/2})_2(Me_2SiO_{2/2})_7(HMeSiO_{2/2})_{11}$
$(MeSiO_{3/2})_1,$ [Chemical Formula 2-2]

The silicon atom-bonded hydrogen atom content is 0.825 wt %. The viscosity is 15 mPa·s.

$HMe_2SiO-(Me_2SiO)_{60}-Me_2SiH.$ [Chemical Formula 2-3]

The silicon atom-bonded hydrogen atom content is 0.043 wt %. The viscosity is 64 mPa·s.

Example 1

The polyorganosiloxane represented by the average formula of [Chemical Formula 1-1] and the polyorganosiloxane represented by the average formula of [Chemical Formula 2-1] were uniformly mixed at room temperature in the blending amounts listed in Table 1. Next, this composition was dispersed in an aqueous solution of 25° C. composed of 0.4 parts by mass of polyoxyethylene alkyl (C12-14) ether and 50 parts by mass of pure water, further uniformly emulsified by a colloid mill, and thereafter, 350 parts by mass was added and diluted to prepare an emulsion. Next, an isopropyl alcohol solution of chloroplatinic acid (in an amount with which the platinum metal in the present composition becomes 10 ppm) was added to the emulsion as a pure water dispersion of polyoxyethylene alkyl (C12-14) ether and stirred, and thereafter this emulsion was allowed to stand at 50° C. for 3 hours to prepare a uniform aqueous suspension of the silicone rubber particles. Next, this water-based suspension was dried with a small spray dryer (manufactured by Ashizawa-Niro) to obtain silicone particles. The properties are shown in Table 1.

Examples 2-4 and Comparative Examples 1 and 2

The raw materials listed in Table 1 were uniformly mixed at room temperature with the blending composition shown in Table 1 to prepare a crosslinkable composition for forming silicone particles. Next, this composition was treated in the same manner as in Example 1 to obtain silicone particles. The properties are shown in Table 1.

TABLE 1

|  |  | Example 1 | Example 2 | Example 3 |
|---|---|---|---|---|
| Charge amount (Parts by mass) | [Chemical formula 1] | 92.5 | 95.8 | 48.4 |
|  | [Chemical formula 1-2] |  |  | 48.4 |
|  | [Chemical Formula 1-3] |  |  |  |
|  | [Chemical Formula 1-4] |  |  |  |
|  | [Chemical Formula 2-1] | 7.5 |  |  |
|  | [Chemical Formula 2-2] |  | 4.2 | 3.2 |
|  | [Chemical Formula 2-3] |  |  |  |
| JIS-A hardness |  | 41 | 39 | 31 |
| SiH residual amount (ppm) |  | 1.9 | 15.8 | 10.2 |
| The average particle diameter of primary particles (μm) |  | 6.8 | 7.3 | 6.9 |
| Powder particle size | Median diameter (μm) | 24 | 25 | 9 |
|  | Degree of dispersion (SD, μm²) | 226 | 250 | 20 |
| Decamethylcyclopentasiloxane mixture solution viscosity (mPa·s) |  | 38 | 21 | 29 |
| Powder oil absorption amount (weight %) | Squalane | 39 | 40 | 44 |
|  | Cetyl ethylhexanoate | 48 | 56 | 59 |
|  | Decamethylcyclopentasiloxane | 203 | 207 | 231 |

TABLE 1-continued

|  |  | Example 4 | Comparative Example 1 | Comparative Example 2 |
|---|---|---|---|---|
| Charge amount (Parts by mass) | [Chemical formula 1] | 54.5 |  |  |
|  | [Chemical formula 1-2] |  | 59.6 |  |
|  | [Chemical Formula 1-3] |  |  | 91.7 |
|  | [Chemical Formula 1-4] |  | 5.4 |  |
|  | [Chemical Formula 2-1] |  | 35.0 | 8.3 |
|  | [Chemical Formula 2-2] |  |  |  |
|  | [Chemical Formula 2-3] | 45.5 |  |  |
| JIS-A hardness |  | 24 | 41 | 47 |
| SiH residual amount (ppm) |  | 1.0 | 373.3 | 25.8 |
| The average particle diameter of primary particles (μm) |  | 7.0 | 6.8 | 7.5 |
| Powder particle size | Median diameter (μm) | 40 | 51 | 13 |
|  | Degree of dispersion (SD, μm$^2$) | 527 | 571 | 62 |
| Decamethylcyclopentasiloxane mixture solution viscosity (mPa·s) |  | 43 | 25 | 28 |
| Powder oil absorption amount (weight %) | Squalane | 42 | 47 | 36 |
|  | Cetyl ethylhexanoate | 62 | 57 | 39 |
|  | Decamethylcyclopentasiloxane | 326 | 167 | 169 |

Hereinafter, formulation examples of the cosmetic material of the present invention, to which the silicone particles as one form of the present invention can be blended, will be shown. However, the present invention is not limited to these examples.

Formulation Example 1: W/O Cream Foundation (Component)
Phase A
Cetyl diglyceryl tris (trimethylsiloxy) silyl ethyl dimethicone
(Note 1) 5.0 parts by mass
2) Dimethicone (Note 2) 4.2 parts by mass
3) Ethylhexyl methoxycinnamate (Note 3) 3.3 parts by mass
4) Caprylyl methicone (Note 4) 3.3 parts by mass
5) Isododecane, (Dimethicone/Bis-isobutyl PPG-20) Crosspolymer (Note 5) 1.5 parts by mass
6) Silicone crosslinked product of Examples 2.0 parts by mass
Phase B
7) Titanium oxide, talc, methicone (Note 6) 4.71 parts by mass
8) Mica, aluminum hydroxide (Note 7) 2.46 parts by mass
9) Iron oxide yellow (Note 8) 0.66 parts by mass
10) Iron oxide red (Note 9) 0.16 parts by mass
11) Iron oxide black (Note 10) 0.006 parts by mass
12) Cetyl diglyceryl tris (trimethylsiloxy) silyl ethyl dimethicone (Note 11) 0.5 parts by mass
13) Caprylylmethicone (Note 12) 3.7 parts by mass
Phase C
14) Purified water 61.5 parts by mass
15) BG 8.0 parts by mass
16) Sodium chloride 1.0 part by mass
Note 1: ES-5600 Silicone Glycerol Emulsifier manufactured by Dow Corning Toray Co., Ltd.
Note 2: PMX-200 SILICONE FLUID 2 CS manufactured by Dow Corning Toray Co., Ltd.
Note 3: Neo Heliopan AV made by Symrise
Note 4: FZ-3196 manufactured by Dow Corning Toray Co., Ltd.
Note 5: EL-8050 ID Silicone Organic Elastomer Blend manufactured by Dow Corning Toray Co., Ltd.
Note 6: SA Titan CR-50 manufactured by Miyoshi Kasei Industry Co., Ltd.
Note 7: SA Exel Mica JP-2 manufactured by Miyoshi Kasei Industry Co., Ltd.
Note 8: SA Yellow UXLO manufactured by Miyoshi Kasei Industry Co., Ltd.
Note 9: SA Red manufactured by Miyoshi Kasei Industry Co., Ltd.
Note 10: SA Black manufactured by Miyoshi Kasei Industry Co., Ltd.
Note 11: ES-5600 Silicone Glycerol Emulsifier manufactured by Dow Corning Toray Co., Ltd.
Note 12: FZ-3196 manufactured by Dow Corning Toray Co., Ltd.

The W/O cream foundation of Formulation Example 1 is adjusted by the following procedure.
1. Mix components 1-6 until uniform.
2. Mix 3 rolls of components 7-13.
3. Mix components 14 to 16.
4. Mix 1 and 2 above.
5. Add 3 above while vigorously stirring 4 above and emulsify.

Formulation Example 2: O/W Foundation (Component)
Phase A
1) Silicone crosslinked product of Examples 18 parts by mass
2) Talc (Note 1) 18 parts by mass
Phase B
3) Purified water 20 parts by mass
4) Glycerin 10 parts by mass
Phase C
5) Sodium polyacrylate, dimethicone (Note 2) 1 part by mass
6) DMDM hydantoin, butyl carbamate propynyl iodide (Note 3) appropriate amount
7) Ethylhexyl salicylate (Note 4) 3 parts by mass
8) Ethylhexyl methoxycinnamate (Note 5) 3 parts by mass
Phase D
9) Purified water 21 parts by mass
Phase E
10) Caprylyl methicone (Note 6) 2 parts by mass
11) Iron oxide black, dimethicone (Note 7) 0.05 parts by mass
12) Iron oxide red, dimethicone (Note 8) 0.1 part by mass
13) Iron oxide yellow, dimethicone (Note 9) 0.25 parts by mass
14) Titanium oxide, talc, dimethicone (Note 10) 3.6 parts by mass
Note 1: Si talc manufactured by Miyoshi Kasei Industry Co., Ltd.
Note 2: RM 2051 Rheology Modifier manufactured by Dow Corning Toray Co., Ltd.
Note 3: Glydant Plus manufactured by Lonza
Note 4: Neo Heliopan OS manufactured by Symrise
Note 5: Escalol 557 manufactured by ISP
Note 6: FZ-3196 manufactured by Dow Corning Toray Co., Ltd.
Note 7: SA-Black BL-100 manufactured by Miyoshi Kasei Industry Co., Ltd.
Note 8: SA-Bengara Cloisonne manufactured by Miyoshi Kasei Industry Co., Ltd.
Note 9: SI-YELLOW-LLXLO manufactured by Miyoshi Kasei Industry Co., Ltd.

Note 10: SI-titanium CR-50 manufactured by Miyoshi Kasei Industry Co., Ltd.

The O/W cream foundation of Formulation Example 2 is adjusted by the following procedure.
1. Mix components 1 and 2.
2. Mix components 3 and 4.
3. Mix 1 and 2 above.
4. Mix components 5-8.
5. Add the component 9 to above 4 and mix.
6. Mix components 10 to 14 until uniform.
7. Mix all components.

Formulation Example 3: W/O BB Cream (Component)
Phase A
1) Lauryl PEG-10 tris(trimethylsiloxy) silyl ethyl dimethicone (Note 1) 3 parts by mass
2) Caprylyl methicone (Note 2) 14 parts by mass
3) Ethylhexyl methoxycinnamate (Note 3) 7.5 parts by mass
4) Hexyl diethylamino hydroxybenzoylbenzoate (Note 4) 1.5 parts by mass
5) Ethylhexyl salicylate 2.5 parts by mass
6) Trimethylsiloxysilicate, polypropylsilsesquioxane (Note 5) 2 parts by mass
7) Silicone crosslinked product of Examples 4 parts by mass
8) Phenyl trimethicone (Note 6) 4 parts by mass
Phase B
9) Glycerin 8 parts by mass
10) Sodium chloride 0.7 parts by mass
11) Purified water 40.8 parts by mass
Phase C
12) Titanium oxide 5.6 parts by mass
13) Iron oxide yellow (Note 7) 0.25 parts by mass
14) Iron oxide red (Note 8) 0.1 parts by mass
15) Iron oxide black (Note 9) 0.05 parts by mass
16) Phenyl trimethicone (Note 10) 5.2 parts by mass
17) Zinc oxide (Note 11) 0.8 parts by mass
18) Lauryl PEG-10 tris (trimethylsiloxy) silyl ethyl dimethicone 1 part by mass
Note 1: ES-5300 Formulation Aid manufactured by Dow Corning Toray Co., Ltd.
Note 2: FZ-3196 manufactured by Dow Corning Toray Co., Ltd.
Note 3: Uvinar MC80N manufactured by BASF
Note 4: Uvinar A Plus Glanular manufactured by BASF
Note 5: MQ-1640 Flake Resin manufactured by Dow Corning Toray Co., Ltd.
Note 6: SH 556 manufactured by Dow Corning Toray Co., Ltd.
Note 7: SA-IOY-8 manufactured by Sanji Kasei Industry Co., Ltd.
Note 8: SA-IOR-8 manufactured by Sanji Kasei Industry Co., Ltd.
Note 9: SA-IOB-8 manufactured by Sanji Kasei Industry Co., Ltd.
Note 10: SH 556 manufactured by Dow Corning Toray Co., Ltd.
Note 11: FINEX-30S-LPT manufactured by SAKAI CHEMICAL INDUSTRY CO., LTD.
Note 12: ES-5300 Formulation Aid manufactured by Dow Corning Toray Co., Ltd.

The W/O BB cream of Formulation Example 3 is adjusted by the following procedure.
1. Mix components 1-8. (Dissolve the UV absorber first and dissolve MQ-1640 in FZ-3196)
2. Mix components 9 to 11.
3. Mix components 12 to 18.
4. Mix 1 and 3 above.
5. While vigorously stirring 1 above, slowly add 2 above and emulsify.

Formulation Example 4: Nonaqueous Foundation (Component)
Phase A
1) Titanium oxide, dimethicone (Note 1) 49.23 parts by mass
2) Iron oxide yellow, dimethicone (Note 2) 9.86 parts by mass
3) Iron oxide red, dimethicone (Note 3) 1.97 parts by mass
4) Iron oxide black, dimethicone (Note 4) 0.55 parts by mass
5) Cetyl diglyceryl tris (trimethylsiloxy) silyl ethyl dimethicone (Note 5) 1.58 parts by mass
6) Caprylylmethicone (Note 6) 15.8 parts by mass
Phase B
7) Silicone crosslinked product of Examples 2 parts by mass
8) Cyclopentasiloxane (Note 7) 13 parts by mass
9) Isododecane, (Acrylates/polytrimethylsiloxy methacrylate) copolymer (Note 8) 5 parts by mass
10) disteardimonium hectorite (Note 9) 1 part by mass
Note 1: SI-titanium CR-50 manufactured by Miyoshi Kasei Industry Co., Ltd.
Note 2: SI-YELLOW-LLXLO manufactured by Miyoshi Kasei Industry Co., Ltd.
Note 3: SA-Bengara Cloisonne manufactured by Miyoshi Kasei Industry Co., Ltd.
Note 4: SA-Black BL-100 manufactured by Miyoshi Kasei Industry Co., Ltd.
Note 5: ES-5600 Silicone Glycerol Emulsifier manufactured by Dow Corning Toray Co., Ltd.
Note 6: FZ-3196 manufactured by Dow Corning Toray Co., Ltd.
Note 7: SH 245 manufactured by Dow Corning Toray Co., Ltd.
Note 8: FA 4002 ID Silicone Acrylate manufactured by Dow Corning Toray Co., Ltd.
Note 9: Bentone® 38 V CG manufactured by Elementis plc The nonaqueous foundation of Formulation Example 4 is adjusted by the following procedure.
1. Mix components 1-6.
2. Mix components 7 to 10.
3. Mix 1 and 2 above.

Formulation Example 5: Compact Foundation (Component)
1) Talc (Note 1) 20 parts by mass
2) Mica (Note 2) 34.6 parts by mass
3) Titanium oxide (Note 3) 10 parts by mass
4) Iron oxide red (Note 4) 1 part by mass
5) Iron oxide yellow (Note 5) 4 parts by mass
6) Iron oxide black (Note 6) 0.4 parts by mass
7) Mica (Note 7) 15 parts by mass
8) Polystyrene (Note 8) 5 parts by mass
9) Squalane 3 parts by mass
10) Octyldodecyl myristate (note 9) 1.2 parts by mass
11) Vaseline 2.5 parts by mass
12) Dimethicone (Note 10) 3.3 parts by mass
13) Silicone crosslinked product of examples 5 parts by mass
Note 1: SI Talc manufactured by Miyoshi Kasei Industry Co., Ltd.
Note 2: SI-SERICITE FSE manufactured by Miyoshi Kasei Industry Co., Ltd.

Note 3: SI-Titan CR-50 manufactured by Miyoshi Kasei Industry Co., Ltd.
Note 4: SA Red manufactured by Miyoshi Kasei Industry Co., Ltd.
Note 5: SA Yellow UXLO manufactured by Miyoshi Kasei Industry Co., Ltd.
Note 6: SA Black manufactured by Miyoshi Kasei Industry Co., Ltd.
Note 7: SA-Excel Mica JP-2 manufactured by Miyoshi Kasei Industry Co., Ltd.
Note 8: Fine pearl 3000 SPQ manufactured by Sumitomo Chemical Co., Ltd.
Note 9: EXCEPARL OD-M manufactured by Kao Corporation
Note 10: SH200-5000cs manufactured by Dow Corning Toray Co., Ltd.

The compact foundation of Formulation Example 5 is adjusted by the following procedure.
1. Mix all of the above.

Formulation Example 6: W/O Skin Cream (Component)
Phase A
1) Lauryl PEG/PPG-18/18 dimethicone (Note 1) 2 parts by weight
2) Bis (hydroxyethoxypropyl) dimethicone (Note 2) 2 parts by mass
3) Isopropyl palmitate (Note 3) 1 part by mass
4) Cyclopentasiloxane (Note 4) 6.5 parts by mass
5) Mineral oil (Note 5) 10 parts by mass
6) Vaseline 1.5 parts by mass
7) Silicone crosslinked product of Examples 5 parts by mass
Phase B
8) Glycerin 5 parts by mass
9) Sodium chloride 1 part by mass
10) Purified water 66 parts by mass
Note 1: 5200 Formulation Aid manufactured by Dow Corning Toray Co., Ltd.
Note 2: 5562 Carbinol Fluid manufactured by Dow Corning Toray Co., Ltd.
Note 3: EXEPARL IPM manufactured by Kao Corporation
Note 4: SH 245 manufactured by Dow Corning Toray Co., Ltd.
Note 5: HICALL K-230 manufactured by KANEDA Co., Ltd.

The W/O skin cream of Formulation Example 6 is adjusted by the following procedure.
1. Mix components 1-7.
2. Mix components 8-10.
3. While vigorously stirring 1 above, slowly add 2 above and emulsify.

Formulation Example 7: Sunscreen Nonaqueous Lotion (Component)
1) Zinc oxide (Note 1) 6 parts by mass
2) Lauryl PEG-10 tris(trimethylsiloxy) silyl ethyl dimethicone (Note 2) 0.5 parts by mass
3) Hexadecane 3.5 parts by mass
4) Ethylhexyl methoxycinnamate (Note 3) 7.5 parts by mass
5) Dimethicone, dimethicone crosspolymer (Note 4) 24 parts by mass
6) Cyclopentasiloxane (Note 5) 60.5 parts by mass
7) Silicone crosslinked product of Examples 2 parts by mass Note 1: FINEX-30S-LPT manufactured by Sakai Chemical Co., Ltd.
Note 2: ES-5300 Formulation Aid manufactured by Dow Corning Toray Co., Ltd.
Note 3: Uvinar MC80N manufactured by BASF
Note 4: 9041 Silicone Elastomer Blend manufactured by Dow Corning Toray Co., Ltd.
Note 5: SH 245 manufactured by Dow Corning Toray Co., Ltd.

The sunscreen nonaqueous lotion of Formulation Example 7 is adjusted by the following procedure.
1. Mix components 1 to 3 (with a bead mill etc.).
2. Add components 4 to 7 to the above ingredients and stir the mixture until uniform.

Formulation Example 8: O/W Wrinkle Care Cream (Component)
Phase A
1) Cyclopentasiloxane (Note 1) 11 parts by mass
2) Silicone crosslinked product 10 parts by mass
3) Lauryl PEG/PPG-18/18 dimethicone (Note 2) 0.5 parts by weight
4) PEG-12 dimethicone (Note 3) 4 parts by mass
Phase B
5) Purified water 72.5 parts by mass
Phase C
6) Polyacrylamide, water, (C13, 14) isoparaffin, Laureth-7 (Note 4) 2 parts by mass
Note 1: SH 245 manufactured by Dow Corning Toray Co., Ltd.
Note 2: 5200 Formulation Aid manufactured by Dow Corning Toray Co., Ltd.
Note 3: OFX-5329 manufactured by Dow Corning Toray Co., Ltd.
Note 4: Simulgel 305 manufactured by SEPPIC S.A.

The O/W wrinkle care cream of Formulation Example 8 is adjusted by the following procedure.
1. Mix components 1-4 until uniform.
2. Mix components 4 and 5 until uniform.
3. Add 1 to 2 above and mix until uniform.

INDUSTRIAL APPLICABILITY

Since silicone particles of the present invention are excellent in dispersibility in ethanol and silicone oil, they are easy to be blended as additives, and when they are blended in cosmetic materials as a cosmetic raw material, their feel can be improved, so that the silicone particle of the present invention can be used for skin cosmetic materials, make-up cosmetic materials, and the like. In addition, by taking advantage of its physical properties, as the application to the electronic materials, the silicone particles of the present invention can also be used for additives such as thermosetting resin composition and thermoplastic resin composition, or for surface lubricant of a plastic film.

The invention claimed is:
1. Silicone particles comprising the reaction product of (A) an organopolysiloxane as a component, wherein:
component (A) has the general formula

$$Me_2HeSiO\text{-}(Me_2SiO)_{135}\text{-}(MeHeSiO)_{0.25}\text{---}SiHeMe_2$$

where Me represents $CH_3-$, and He represents $CH_2{=}CH-C_4H_8-$;
a content of hydrogen bonded to a silicon atom per unit mass is 20 ppm or less; and a silicon atom in component (A) is crosslinked with another silicon atom in the reaction product via a hexenyl (He) group.

2. The silicone particles according to claim 1, wherein a powder particle diameter is 1 to 50 μm as measured by a laser diffraction scattering method.

3. The silicone particles according to claim 1, wherein JIS-A hardness is 70 or less as measured by curing in a sheet form a pre-cured crosslinkable composition for forming the silicone particles.

4. The silicone particles according to claim 3, wherein a relationship between the JIS-A hardness (Vα) measured by curing in a sheet form the pre-cured crosslinkable composition for forming the silicone particles and a powder particle diameter measured by a laser diffraction scattering method (Vβ) satisfies: Vα×Vβ≤1,200.

5. The silicone particles according to claim 1, which are a cosmetic raw material.

6. A cosmetic product comprising the silicone particles according to claim 5.

7. The silicone particles according to claim 1, which are a resin compounding agent.

8. A paint containing the silicone particles according to claim 7.

9. The silicone particles according to claim 1, wherein the He group content of component (A) is 0.97 wt %.

10. The silicone particles according to claim 1, wherein the viscosity of component (A) is 420 mPa·s.

* * * * *